US007776810B2

(12) United States Patent
Jordan, IV et al.

(10) Patent No.: US 7,776,810 B2
(45) Date of Patent: Aug. 17, 2010

(54) COMPOSITIONS CONTAINING IONIC LIQUID ACTIVES

(75) Inventors: Glenn Thomas Jordan, IV, Indian Springs, OH (US); Stacie Ellen Hecht, West Chester, OH (US); Kenneth Nathan Price, Wyoming, OH (US); Patricia Sara Berger, Cincinnati, OH (US); Yousef Georges Aouad, Cincinnati, OH (US); Jean Wevers, Steenhuffel (BE); Dennis Allen Beckholt, Fairfield, OH (US); Frank William Denome, Cincinnati, OH (US); Kevin George Goodall, Tervuren (BE); Jose Luis Vega, Cincinnati, OH (US); Michael Stanford Showell, Cincinnati, OH (US); Kenneth Richard Seddon, Donaghadee (GB); Harambage Quintus Nimal Gunaratne, Belfast (GB)

(73) Assignee: The Procter & Gamble Company, Cincinnati, OH (US)

( * ) Notice: Subject to any disclaimer, the term of this patent is extended or adjusted under 35 U.S.C. 154(b) by 909 days.

(21) Appl. No.: 11/263,383

(22) Filed: Oct. 31, 2005

(65) Prior Publication Data

US 2006/0094620 A1 May 4, 2006

Related U.S. Application Data

(60) Provisional application No. 60/624,128, filed on Nov. 1, 2004.

(51) Int. Cl.
*C11D 1/62* (2006.01)
*C11D 3/20* (2006.01)
*C11D 3/26* (2006.01)

(52) U.S. Cl. .................. 510/329; 510/296; 510/336; 510/337; 510/439; 510/504; 510/505; 510/515

(58) Field of Classification Search ................ 510/327, 510/328, 329, 330, 296, 336, 337, 351, 357, 510/439, 504
See application file for complete search history.

(56) References Cited

U.S. PATENT DOCUMENTS

| | | | |
|---|---|---|---|
| 3,282,728 A | 11/1966 | Lacroux et al. | |
| 4,126,573 A | 11/1978 | Johnston et al. | |
| 4,189,311 A | 2/1980 | Laqua et al. | |
| 4,689,168 A | 8/1987 | RequeJo et al. | |
| 4,717,507 A | 1/1988 | Schwadtke et al. | |
| 4,756,850 A | 7/1988 | Nayar | |
| 5,705,466 A | 1/1998 | Baillely | |
| 5,731,101 A | 3/1998 | Sherif et al. | |
| 5,827,602 A | 10/1998 | Koch et al. | |
| 6,048,388 A | 4/2000 | Schwarz | |
| 6,086,785 A | 7/2000 | Roesler et al. | |
| 6,277,808 B1 | 8/2001 | Tcheou et al. | |
| 6,288,281 B1 | 9/2001 | Nemeth et al. | |
| 6,339,182 B1 | 1/2002 | Munson et al. | |
| 6,372,829 B1 | 4/2002 | Lamanna et al. | |
| 6,479,446 B1 | 11/2002 | Sherry et al. | |
| 6,521,584 B1 | 2/2003 | Soldanski et al. | |
| 6,767,882 B1 | 7/2004 | Jagannath et al. | |
| 6,808,557 B2 | 10/2004 | Holbrey et al. | |
| 6,824,599 B2 | 11/2004 | Swatlowski et al. | |
| 2001/0014654 A1 | 8/2001 | Davister et al. | |
| 2004/0005286 A1 | 1/2004 | Giroud | |
| 2004/0007693 A1 | 1/2004 | Moulton et al. | |
| 2004/0035293 A1 | 2/2004 | Davis, Jr. | |
| 2004/0054231 A1 | 3/2004 | Abbott et al. | |
| 2004/0077519 A1 | 4/2004 | Price | |
| 2004/0096932 A1 | 5/2004 | Kragl et al. | |
| 2004/0097755 A1 | 5/2004 | Abbott et al. | |
| 2004/0133058 A1 | 7/2004 | Arlt et al. | |
| 2004/0142840 A1 * | 7/2004 | de Buzzaccarini et al. | .. 510/296 |
| 2004/0198902 A1 | 10/2004 | Yui et al. | |
| 2006/0090777 A1 | 5/2006 | Hecht | |
| 2006/0094615 A1 | 5/2006 | Hecht | |
| 2006/0094616 A1 | 5/2006 | Hecht | |
| 2006/0094617 A1 | 5/2006 | Price | |
| 2006/0094620 A1 | 5/2006 | Jordan, IV et al. | |

(Continued)

FOREIGN PATENT DOCUMENTS

CN 1081629 7/1999

(Continued)

OTHER PUBLICATIONS

U.S. Appl. No. 11/263,391, filed Oct. 31, 2005, Price.

(Continued)

*Primary Examiner*—Gregory R Del Cotto
(74) *Attorney, Agent, or Firm*—Stephen T. Murphy; Andrew J. Mueller; Leonard W. Lewis

(57) ABSTRACT

Compositions comprising an ionic liquid active composed of an ion active and an ionic liquid-forming counter ion, wherein the ion active is capable of delivering a fabric treating benefit, a surface treating benefit, and/or an air treating benefit. The compositions are substantially free of added water and have a viscosity less than about 5000 mPa·s at room temperature. The compositions are easily diluted with water and/or organic solvent, without formation a gel phase during the dilution process. Various products, especially a unit dose product, made with such compositions are also disclosed.

4 Claims, No Drawings

U.S. PATENT DOCUMENTS

2006/0094621 A1   5/2006   Jordan, IV

FOREIGN PATENT DOCUMENTS

| DE | 101 37 047 A1 | 2/2003 |
|---|---|---|
| EP | 0 723 006 A | 7/1996 |
| EP | 1 454 978 A | 9/2004 |
| FR | 1296756 | 5/1962 |
| FR | 2 101 710 A | 3/1972 |
| GB | 1 014 539 A | 12/1965 |
| JP | 3064368 | 3/1991 |
| JP | 5178798 A | 7/1993 |
| JP | 06009767 A2 | 1/1994 |
| JP | 10265674 A | 6/1998 |
| JP | 11084603 A2 | 3/1999 |
| JP | 2915208 B2 | 7/1999 |
| WO | WO 98/55581 A | 12/1998 |
| WO | WO 00/01793 A | 1/2000 |
| WO | WO 01/19200 A1 | 3/2001 |
| WO | WO 01/77486 A1 | 10/2001 |
| WO | WO 02/34722 A1 | 5/2002 |
| WO | WO 02/38784 | 5/2002 |
| WO | WO 03/074494 A1 | 9/2003 |
| WO | WO 2004/022670 A1 | 3/2004 |
| WO | WO 2004/035018 A2 | 4/2004 |
| WO | WO 2004/067739 A2 | 8/2004 |

OTHER PUBLICATIONS

U.S. Appl. No. 10/345,569, filed Feb. 1, 2006, Hehct.

XP 002375958, 1993, Anufrieva, V, Chem. Abstract.

XP 002375959, 1991, Beilstein Institut zur Forderung, Chem. Abstract.

XP 002375960, 1989, J. Amer. Chem, Chem. Abstract.

XP 002375961, 1990, Beilstein Institut zur Forderung, Chem. Abstract.

XP 002375962, 1994, Beilstein Instut zur Forderung, Chem. Abstract.

XP 002375963, 1994, Beilstein Institut zur Forderung, Chem. Abstract.

John S Wilks, Air and Water Stable 1-Ethyl-3-methylimidazolium Based Ionic Liquids, The rank J. Seller Research Laboratory, United States Air Force Academy, Colorado, US, 1992, pp. 965-967.

J D Holbrey, Clean Products and Processes (1999) pp. 223, 236.

Richard Swatloski, Dissolution of Cellose with Ionic Liquids, Center for Green Manufacturing and Department of Chemistry, the University of Alabama, (2002) pp. 4974-4975, Feb. 2002.

David Bradley, Super Solvents, Technology Ireland, Sep. 1999.

Brycki, Szafran, Formation of the Homoconjugated Cation (N-0 H O-N)+ of *N*-Dodecyl-*N, N*-Dimethylamine Oxide in Carbon Tetrachloride, Journal of Molecular Structure, 239 (1190) pp. 1-11, (1990).

Golding, J, Methanesulfonate and *p*-toluenesulfonate salts of the *N*-methyl-*N*-alkylpyrrolidinium and quarternary ammonium cations: novel low cost ionic liquids, Centre for Green Chemistry, School of Chemistry, Monash University, pp. 223-229, Apr. 2002.

International Search Report, Apr. 2002.

* cited by examiner

COMPOSITIONS CONTAINING IONIC LIQUID ACTIVES

CROSS REFERENCE TO RELATED APPLICATIONS

This application claims priority under 35 U.S.C. §119(e) from Provisional Application Ser. No. 60/624,128, filed on Nov. 1, 2004.

FIELD OF THE INVENTION

The present invention is directed to compositions containing ionic liquid actives for providing a fabric treating benefit, a surface treating benefit, and/or an air treating benefit. The present invention is also directed to the advantageous diluting process of such composition without formation of a gel phase during the dilution process. The present invention further relates to various products, especially a unit dose product, made with such compositions.

BACKGROUND OF THE INVENTION

In recent years, ionic liquids have been extensively evaluated as environmental-friendly or "green" alternatives to conventional organic solvents for a broad range of organic synthetic applications. Ionic liquids offer some unique characteristics that distinguish them from conventional organic solvents, such as no effective vapor pressure, a broad liquid range, high polarity and charge density, can be either hydrophobic or hydrophilic, and unique solvating properties.

One widely studied class of ionic liquids includes imidazolium salts, such as 1-butyl-3-methylimidazolium hexafluorophosphate, also known as [bmim][$PF_6$]. Other well known ionic liquids include 1-ethyl-3-methylimidazolium chloride-aluminium (III) chloride, which is usually referred to as [emim]Cl—$AlCl_3$; and N-butyl pyridinium chloride aluminium (III) chloride, which is usually referred to as [Nbupy]Cl—$AlCl_3$. A broad range of ionic liquids have also been investigated in the following references: U.S. Pat. Nos. 6,048,388; 5,827,602; US 2003/915735A1; US 2004/0007693A1; US 2004/0035293A1; WO 02/26701; WO 03/074494; WO 03/022812; and WO 04/016570.

Published PCT Application WO 2004/003120 discloses ionic liquid based products suitable for use in surface or air treating compositions, and ionic liquid cocktails containing three or more different and charged ionic liquid components. The products are particularly useful in various consumer product applications, such as home care, air care, surface cleaning, laundry and fabric care applications.

It is desirable to take advantage of the various unique characteristics of the ionic liquid to form compact or concentrated products. Specifically, it is desirable to form compositions comprising an ionic liquid active composed of an ion active and an ionic liquid-forming counter ion, wherein the ion active is capable of delivering a fabric treating benefit, a surface treating benefit, and/or an air treating benefit. The composition in its supercompact (i.e., highly concentrated) form is substantially free of added water.

Additionally, it is desirable that such compositions have a low viscosity of less than about 5000 mPa·s at room temperature. It is also desirable that such compositions can be easily diluted with water and/or solvents without formation of a gel phase (i.e., a high viscosity phase) during the dilution process.

SUMMARY OF THE INVENTION

One aspect of the present invention relates to a concentrated composition, comprising an ionic liquid active composed of an ion active and an ionic liquid-forming counter ion, wherein the ion active is capable of delivering a fabric treating benefit, a surface treating benefit, and/or an air treating benefit, and wherein the composition is substantially non-aqueous.

Another aspect of the present invention relates to a composition comprising from about 1 to about 75 weight percent of the ionic liquid active composed of an ion active and an ionic liquid-forming counterion, from about 0.01 to about 50 weight percent water and the balance, adjuncts.

The present invention also relates to a unit dose product comprising a unit dose package and the ionic liquid-containing composition in the package.

Additionally, the compositions of the present invention are advantageous in a process for preparing a wash liquor because the composition, upon dilution, does not exhibit a gel phase throughout the process.

Additional embodiments of the compositions and processes are described in further detail in the following detailed description.

DETAILED DESCRIPTION OF THE INVENTION

The compositions according to the present invention comprise an ionic liquid active composed of an ion active and an ionic liquid-forming counter ion. As used herein, the term "ion active" means the ion (cationic or anionic) form of an active or a benefit agent capable of delivering benefits, for example, a fabric treating benefit, a surface treating benefit, and/or an air treating benefit, to a target substrate. The ion active retains the capability of delivering such benefits.

The ion active which forms the ionic liquid active is any ionic moiety which provides the desired treating benefit to a target object or a target surface. Within the present context, fabric treating refers generally to the cleaning, refreshing and/or care of any textile material or product, including, but not limited to, loose or free fibers, yarns (including threads), woven textiles, nonwoven textiles, knitted textiles, articles, and the like. Fabric articles include, but are not limited to, garments, components used in the manufacture of garments, carpets, upholstery, and the like. Additionally, such fabrics may be formed of any natural, man-made or synthetic material, or a combination thereof. Surface treating refers generally to the cleaning, refreshing and/or care of any non-fabric solid surface material, including, but not limited to, dishes, utensils and other items intended for food contact, and hard surfaces, for example, floors, counters, appliances, sinks, tubs, toilets, tiles and the like. Air treating refers to cleaning and/or refreshing of environmental air, typically in an enclosed area.

Examples of suitable ion actives include, but are not limited to, the ion form of surfactants, bleaches, bleach activators, builders, antimicrobial agents, softeners, dyes, dye fixatives, optical brighteners, or combinations thereof.

The ionic active may be anionic or cationic, as necessary for the desired benefit, and is typically derived from a salt or acid of a known benefit agent. For example, if a conventional benefit agent in salt form is of the formula $X^+Y^-$ and the anion $Y^-$ provides the desired fabric, surface or air treating activity, then the anionic form of the benefit agent is employed in the ionic liquid active. Examples of suitable anionic actives include, but are not limited to, anionic phosphate builders, anionic linear alkyl sulfate and sulfonate detersive surfactants, anionic alkylated and alkoxylated sulfate and sulfonate detersive surfactants, anionic perborate, percarbonate and peracid bleaches, and the like. Alternatively, if the cation $X^+$ of the conventional benefit agent in the salt form of the formula $X^+Y^-$ provides the desired fabric, surface or air treating activity, then the cationic form of the benefit agent is employed in the ionic liquid active. Examples of suitable cationic actives include, but are not limited to, cationic quaternary ammonium antimicrobial agents, cationic quaternary ammonium fabric softeners, cationic quaternary ammonium surfactants, and the like. Examples of suitable zwitterionic actives include, but are not limited to, amine oxide surfactants and betaine surfactants.

Additionally, a conventional nonionic or zwitterionic benefit agent can be converted to an ionic active by ionic functionalization with a cationic functional group (such as a trimethyl ammonium alkyl group) or an anionic functional group (such as a sulfate group). Alternatively, a zwitterinoic benefit agent can be ionized by pH changes to the compositions to below the pKa of the zwitterionic active, resulting in a cationic form of the benefit agent.

Furthermore, the anionic form of an benefit agent can be combined with a cationic form of another benefit agent, for example, the ionic liquid actives may compose pairings of a cationic fabric softener, a cationic antimicrobial, or a cationic surfactant with an anionic bleach activator or an anionic surfactant.

In some embodiments, the ionic active is formed from known benefit agents which are insoluble or exhibit low solubility when employed in conventional fabric, surface or air treating compositions. The ion active, upon functionalization or ionization, will be combined with selected ionic liquid-forming counter ions to form the salt having ionic liquid characteristics, such as low melting point and/or flowability as described below.

Ionic liquid as used herein refers to a salt that has a melting temperature of about 100° C. or less, or, in an alternative embodiment, has a melting temperature of about 60° C. or less, or, in yet another alternative embodiment, has a melting temperature of about 40° C. or less. In other embodiments, the ionic liquids exhibit no discernible melting point (based on DSC analysis) but are "flowable" at a temperature of about 100° C. or below, or, in another embodiment, are "flowable" at a temperature of from about 20 to about 80° C., i.e., the typical fabric or dish washing temperatures. As used herein, the term "flowable" means that the ionic liquid exhibits a viscosity of less than about 10,000 mPa·s at the temperatures as specified above.

It should be understood that the terms "ionic liquid", "ionic compound", and "IL" encompass ionic liquids, ionic liquid composites, and mixtures (or cocktails) of ionic liquids. The ionic liquid can comprise an anionic IL component and a cationic IL component. When the ionic liquid is in its liquid form, these components may freely associate with one another (i.e., in a scramble). As used herein, the term "cocktail of ionic liquids" refers to a mixture of two or more, preferably at least three, different and charged IL components, wherein at least one IL component is cationic and at least one IL component is anionic. Thus, the pairing of three cationic and anionic IL components in a cocktail would result in at least two different ionic liquids. The cocktails of ionic liquids may be prepared either by mixing individual ionic liquids having different IL components, or by preparing them via combinatorial chemistry. Such combinations and their preparation are discussed in further detail in US 2004/0077519A1 and US 2004/0097755A1. As used herein, the term "ionic liquid composite" refers to a mixture of a salt (which can be solid at room temperature) with a proton donor Z (which can be a liquid or a solid) as described in the references immediately above. Upon mixing, these components turn into a liquid at about 100° C. or less, and the mixture behaves like an ionic liquid.

Nonlimiting examples of anions and cations suitable for use in the ionic liquids for the present invention are disclosed below.

Anions

Anions suitable for use in the ionic liquids of the present invention include, but are not limited to, the following materials:

(1) Alkyl sulfates (AS), alkoxy sulfates and alkyl alkoxy sulfates, wherein the alkyl or alkoxy is linear, branched or mixtures thereof; furthermore, the attachment of the sulfate group to the alkyl chain can be terminal on the alkyl chain (AS), internal on the alkyl chain (SAS) or mixtures thereof: nonlimiting examples include linear $C_{10}$-$C_{20}$ alkyl sulfates having formula:

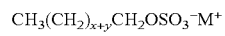
$$CH_3(CH_2)_{x+y}CH_2OSO_3^-M^+$$

wherein x+y is an integer of at least 8, preferably at least about 10; $M^+$ is a cation selected from the cations of the ionic liquids as described in detail herein; or linear $C_{10}$-$C_{20}$ secondary alkyl sulfates having formula:

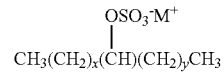
$$\begin{array}{c} OSO_3^-M^+ \\ | \\ CH_3(CH_2)_x(CH)(CH_2)_yCH_3 \end{array}$$

wherein x+y is an integer of at least 7, preferably at least about 9; x or y can be 0, $M^+$ is a cation selected from the cations of the ionic liquids as described in detail herein; or C10-C20 secondary alkyl ethoxy sulfates having formula:

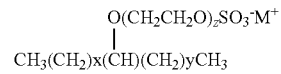
$$\begin{array}{c} O(CH_2CH_2O)_zSO_3^-M^+ \\ | \\ CH_3(CH_2)x(CH)(CH_2)yCH_3 \end{array}$$

wherein x+y is an integer of at least 7, preferably at least about 9; x or y can be 0, $M^+$ is a cation selected from the cations of the ionic liquids as described in detail herein; nonlimiting examples of alkoxy sulfate include sulfated derivatives of commercially available alkoxy copolymers, such as Pluronics® (from BASF);

(2) Mono- and di-esters of sulfosuccinates: nonlimiting examples include saturated and unsaturated $C_{12-18}$ monoester sulfosuccinates, such as lauryl sulfosuccinate available as Mackanate LO-100® (from The McIntyre Group); saturated and unsaturated $C_6$-$C_{12}$ diester sulfosuccinates, such as dioctyl ester sulfosuccinate available as Aerosol OT® (from Cytec Industries, Inc.);

(3) Methyl ester sulfonates (MES);

(4) Alkyl aryl sulfonates, nonlimiting examples include tosylate, alkyl aryl sulfonates having linear or branched, saturated or unsaturated $C_8$-$C_{14}$ alkyls; alkyl benzene sulfonates (LAS) such as $C_{11}$-$C_{18}$ alkyl benzene sulfonates;

(5) Alkyl glycerol ether sulfonates having 8 to 22 carbon atoms in the alkyl moiety;

(6) Diphenyl ether (bis-phenyl) derivatives: Nonlimiting examples include triclosan (2,4,4'-trichloro-2'-hydroxydiphenyl ether) and diclosan (4,4'-dichloro-2-hydroxydiphenyl ether), both are available as Irgasan® from Ciba Specialty Chemicals;

(7) Linear or cyclic carboxylates: nonlimiting examples include Citrate, lactate, tartarate, succinate, alkylene succinate, maleate, gluconate, formate, cinnamate, benzoate, acetate, salicylate, phthalate, aspartate, adipate, acetyl salicylate, 3-methyl salicylate, 4-hydroxy isophthalate, dihydroxyfumarate, 1,2,4-benzene tricarboxylate, pentanoate and mixtures thereof;

(8) Mid-chain branched alkyl sulfates (HSAS), mid-chain branched alkyl aryl sulfonates (MLAS) and mid-chain branched alkyl polyoxyalkylene sulfates; nonlimiting examples of MLAS are disclosed in U.S. Pat. No. 6,596,680; U.S. Pat. No. 6,593,285; and U.S. Pat. No. 6,202,303;

(9) Sarcosinates having the general formula $RCON(CH_3)CH_2CO_2^-$, wherein R is an alkyl from about $C_{8-20}$; nonlimiting examples include ammonium lauroyl sarcosinate, available as Hamposyl AL-30® from Dow Chemicals and sodium oleoyl sarcosinate, available as Hamposyl O® from Dow Chemical;

(10) Sulfated and sulfonated oils and fatty acids, linear or branched, such as those sulfates or sulfonates derived from potassium coconut oil soap available as Norfox 1101® from Norman, Fox & Co. and Potassium oleate from Chemron Corp.;

(11) Fatty acid ester sulfonates having the formula:

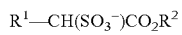

wherein $R^1$ is linear or branched $C_8$ to $C_{18}$ alkyl, and $R^2$ is linear or branched $C_1$ to $C_6$ alkyl;

(12) Sweetener derived anions: saccharinate and acesulfamate;

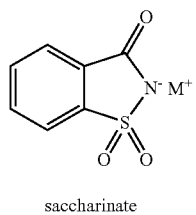 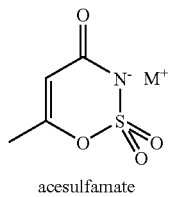

saccharinate    acesulfamate wherein M+ is a cation selected from the cations of the ionic liquids as described herein;

(13) Ethoxylated amide sulfates; sodium tripolyphosphate (STPP); dihydrogen phosphate; fluroalkyl sulfonate; bis-(alkylsulfonyl) amine; bis-(fluoroalkylsulfonyl)amide; (fluroalkylsulfonyl)(fluoroalkylcarbonyl)amide; bis(arylsulfonyl)amide; carbonate; tetrafluorborate ($BF_4^-$); hexaflurophosphate ($PF_6^-$);

(14) Anionic bleach activators having the general formula:

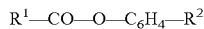

wherein $R^1$ is $C_8$-$C_{18}$ alkyl, $C_8$-$C_{18}$ amino alkyl, or mixtures thereof, and $R^2$ is sulfonate or carbonate; nonlimiting examples such as:

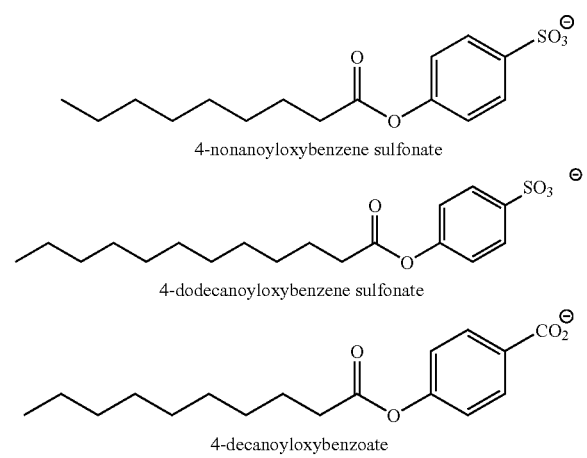

4-nonanoyloxybenzene sulfonate 4-dodecanoyloxybenzene sulfonate 4-decanoyloxybenzoate are disclosed in U.S. Pat. Nos. 5,891,838; 6,448,430; 5,891,838; 6,159,919; 6,448,430; 5,843,879; 6,548,467.

Cations

Cations suitable for use in the ionic liquids of the present invention include, but are not limited to, the following materials:

(a) Cations (i.e., in the protonated, cationic form) of amine oxides, phosphine oxides, or sulfoxides: nonlimiting examples include amine oxide cations containing one $C_{8-18}$ alkyl moiety and 2 moieties selected from the group consisting of $C_{1-3}$ alkyl groups and $C_{1-3}$ hydroxyalkyl groups; phosphine oxide cations containing one $C_{10-18}$ alkyl moiety and 2 moieties selected from the group consisting of $C_{1-3}$ alkyl groups and $C_{1-3}$ hydroxyalkyl groups; and sulfoxide cations containing one $C_{10-18}$ alkyl moiety and a moiety selected from the group consisting of $C_{1-3}$ alkyl and $C_{1-3}$ hydroxyalkyl moieties; in some embodiments, the amine oxide cations have the following formula:

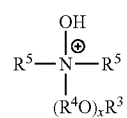

wherein $R^3$ is an $C_{8-22}$ alkyl, $C_{8-22}$ hydroxyalkyl, $C_{8-22}$ alkyl phenyl group, and mixtures thereof; $R^4$ is an $C_{2-3}$ alkylene or $C_{2-3}$ hydroxyalkylene group or mixtures thereof; x is from 0 to about 3; and each $R^5$ is independently an $C_{1-3}$ alkyl or $C_{1-3}$ hydroxyalkyl group or a polyethylene oxide group containing an average of from about 1 to about 3 ethylene oxide groups; the $R^5$ groups may be attached to each other, e.g., through an oxygen or nitrogen atom, to form a ring structure; other exemplary amine oxide cations include $C_{10}$-$C_{18}$, $C_{10}$, $C_{10}$-$C_{12}$, and $C_{12}$-$C_{14}$ alkyl dimethyl amine oxide cations, and $C_8$-$C_{12}$ alkoxy ethyl dihydroxy ethyl amine oxide cations;

(b) Betaines having the general formula:

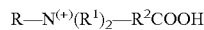

wherein R is selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring treated as equivalent to about 2 carbon atoms, and similar structures interrupted by amido or ether linkages; each $R^1$ is an alkyl group containing from 1 to about 3 carbon atoms; and $R^2$ is an alkylene group containing from 1 to about 6 carbon atoms; nonlimiting examples of betaines include dodecyl dimethyl betaine, acetyl dimethyl betaine, dodecyl amidopropyl dimethyl betaine, tetradecyl dimethyl betaine, tetradecyl amidopropyl dimethyl betaine, dodecyl dimethyl ammonium hexanoate; and amidoalkylbetaines which are disclosed in U.S. Pat. Nos. 3,950,417; 4,137,191; and 4,375,421; and British Patent GB No. 2,103,236; in another embodiment, the cation may be a sulfobetaine, which are disclosed in U.S. Pat. No. 4,687,602;

(c) Diester quaternary ammonium (DEQA) cations of the type:

wherein each R substituent is selected from hydrogen; $C_1$-$C_6$ alkyl or hydroxyalkyl, preferably methyl. ethyl, propyl, or hydroxyethyl, and more preferably methyl; poly ($C_1$-$C_3$ alkoxy), preferably polyethoxy; benzyl; or a mixture thereof; m is 2 or 3; each n is from 1 to about 4; each Y is —O—(O)C—, —C(O)—O—, —NR—C(O)—, or —C(O)—NR—; with the proviso that when Y is —O—(O)C— or —NR—C(O)—, the sum of carbons in each $R^1$ plus one is $C_{12}$-$C_{22}$, preferably $C_{14}$-$C_{20}$, with each $R^1$ being a hydrocarbyl, or substituted hydrocarbyl group; in one embodiment, the DEQA cation is an alkyl dimethyl hydroxyethyl quaternary ammonium as discussed in U.S. Pat. No. 6,004,922; in another embodiment, the DEQA cation has the general formula:

$R_3N^+CH_2CH(YR^1)(CH_2YR^1)$ wherein each Y, R, $R^1$ have the same meanings as before; in yet another embodiment, the DEQA cation is $[CH_3]_3 N^{(+)} [CH_2CH(CH_2(O)CR^1)O(O)CR^1]$ wherein each $R^1$ is in the range of $C_{15}$ to $C_{19}$;

(d) Alkylene quaternary ammonium cations having the formula:

wherein each m is 2 or 3; each R is independently an alkyl or hydroxyalkyl $C_1$-$C_6$ moiety, preferably methyl, ethyl, propyl or hydroxyethyl, and more preferably methyl; each $R^1$ is independently a linear or branched, saturated or unsaturated $C_6$-$C_{22}$ alkyl or alkoxy moiety, preferably $C_{14}$-$C_{20}$ moiety, but no more than one $R^1$ being less than about $C_{12}$ and then the other $R^1$ is at least about $C_{16}$; or hydrocarbyl or substituted hydrocarbyl moiety, preferably $C_{10}$-$C_{20}$ alkyl or alkenyl, most preferably $C_{12}$-$C_{18}$ alkyl or alkenyl; in one embodiment, the cation is dialkylenedimethyl ammonium, such as dioleyldimethyl ammonium available from Witco Corporation under the tradename Adogen® 472; in another embodiment, the cation monoalkenyltrimethyl ammonium, such as monooleyltrimethyl ammonium, monocanolatrimethyl ammonium, and soyatrimethyl ammonium;

(e) Difatty amido quaternary ammonium cations such as:

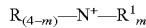

wherein R and $R^1$ are as defined in cation (e) above, $R^2$ and $R^3$ are $C_1$-$C_6$ alkylene moieties; for example, difatty amido quats are commercially available from Witco under the Varisoft® tradename;

(f) $C_{8-22}$ quaternary surfactants such as isostearyl ethyl imidonium available in its ethosulfate salt form as Schercoquat IIS® from Scher Chemicals, Inc., quaternium-52 obtainable as Dehyquart SP® from Cognis Corporation, and dicoco dimethyl ammonium available in its chloride salt form as Arquad 2C-75® from Akzo Nobel Surface Chemistry LLC;

(g) Cationic esters such as discussed in U.S. Pat. Nos. 4,228,042, 4,239,660, 4,260,529 and U.S. Pat. No. 6,022,844;

(h) 4,5-dichloro-2-n-octyl-3-isothiazolone, which is obtainable as Kathon® from Rohm and Haas;

(i) Quaternary amino polyoxyalkylene derivatives (choline and choline derivatives);

(j) Alkyl oxyalkylene cations;

(k) Alkoxylate quaternary ammoniums (AQA) as discussed in U.S. Pat. No. 6,136,769;

(l) Substituted and unsubstituted pyrrolidinium, imidazolium, benzimidazolium, pyrazolium, benzpyrazolium, thiazolium, benzthiazolium, oxazolium, benzoxazolium, isoxazolium, isothiazolium, imdazolidenium, Guanidinium, indazolium, quinuclidinium, triazolium, isoquinuclidinium, piperidinium, morpholinium, pyridazinium, pyrazinium, triazinium, azepinium, diazepinium, pyridinium, piperidonium, pyrimidinium, thiophenium; phosphonium; in one embodiment, the cation is an substituted imidazolium cation having the formula:

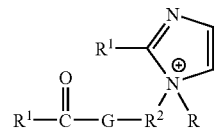

wherein each R and $R^1$ are as defined in cation (e) above; each $R^2$ is a $C_1$-$C_6$ alkylene group, preferably an ethylene group; and G is an oxygen atom or an —NR— group; for example, the cation 1-methyl-1-oleylamidoethyl-2-oleylimidazolinium is available commercially from the Witco Corporation under the trade name Varisoft® 3690; in another embodiment, the cation is alkylpyridinium cation having the formula:

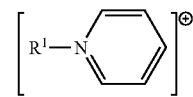

wherein $R^1$ is an acyclic aliphatic $C_8$-$C_{22}$ hydrocarbon group; in another embodiment, the cation is an alkanamide alkylene pyridinium cation having the formula:

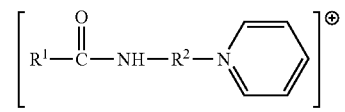

wherein $R^1$ is a linear or branched, saturated or unsaturated $C_6$-$C_{22}$ alkyl or alkoxy moiety, or a hydrocarbyl or substituted hydrocarbyl moiety, and $R^2$ is a $C_1$-$C_6$ alkylene moiety;

(m) Cationic bleach activators having a quaternary ammonium moiety including but not limited to

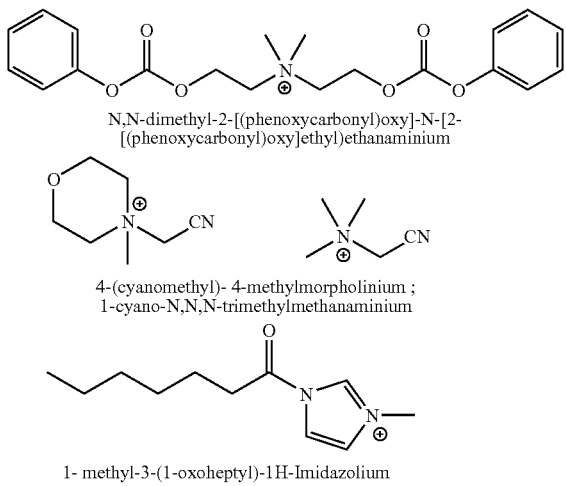

N,N-dimethyl-2-[(phenoxycarbonyl)oxy]-N-[2-[(phenoxycarbonyl)oxy]ethyl)ethanaminium 4-(cyanomethyl)-4-methylmorpholinium;
1-cyano-N,N,N-trimethylmethanaminium 1-methyl-3-(1-oxoheptyl)-1H-Imidazolium these and other cationic bleach activators suitable for use herein as cations of the ionic liquids are disclosed in U.S. Pat. Nos. 5,599,781, 5,686,015, 5,686,015, WO 95/29160, U.S. Pat. Nos. 5,599,781, 5,534,179, EP 1 253 190 A1, U.S. Pat. Nos. 6,183,665, 5,106,528, 5,281,361, and Bulletin de la Societe Chimique de France (1973), (3)(Pt. 2), 1021-7;

(n) Cationic anti-microbial agents, such as cetyl pyridinium, chlorohexidine and domiphen.

(o) Alkylated caffeine cations, such as

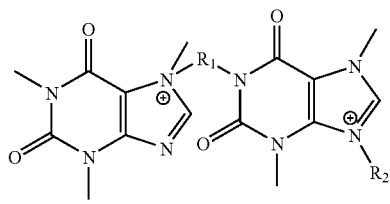

wherein $R_1$ and $R_2$ are C1 to C12 alkyl or alkylene groups.

Thus, the ionic liquids suitable for use herein may have various anionic and cationic combinations. The ionic species can be adjusted and mixed such that properties of the ionic liquids can be customized for specific applications, so as to provide the desired solvating properties, viscosity, melting point, and other properties, as desired. These customized ionic liquids have been referred to as "designer solvents".

In one embodiment, the ionic liquid may be a composite which comprises a mixture of a salt (which can be solid at room temperature) with a proton donor Z (which can be a liquid or a solid) as described above. Upon mixing, these components turn into a liquid at about 100° C. or less, and the mixture behaves like an ionic liquid. Ionic liquid composites comprising various salts and proton donors are disclosed in WO 02/26701 and US 2004/0077519A1.

In some embodiments, ionic liquids (undiluted with adjuncts, co-solvents or free water) employed herein have viscosities of less than about 2000 mpa·s, preferably less than about 750 mPa·s, as measured at 20° C. In some embodiments, the viscosity of undiluted ionic liquids are in the range from about 0.1 to about 500 mPa·s, preferably from about 0.5 to about 300 mPa·s, and more preferably from about 1 to about 250 mPa·s.

The viscosities of the ionic fluids and compositions containing them can be measured on a Brookfield viscometer model number LVDVII+ at 20° C., with spindle no. S31 at the appropriate speed to measure materials of different viscosities. Typically, the measurement is done at a speed of 12 rpm to measure products of viscosity greater than about 1000 mPa·s; 30 rpm to measure products with viscosities between about 500 mPa·s to about 1000 mPa·s; and 60 rpm to measure products with viscosities less than about 500 mPa·s. The undiluted state is prepared by storing the ionic liquids or cocktails in a desiccator containing a desiccant (e.g. calcium chloride) at room temperature for at least about 48 hours prior to the viscosity measurement. This equilibration period unifies the amount of innate water in the undiluted samples.

Advantageously, the ionic liquid active is in liquid form. Thus, the ionic liquid active is a means for providing highly concentrated functional actives that are conventionally only available in solid or paste form, or require large amounts of diluents or solvents to form liquids. In some embodiments, the need for other solvents and/or diluents can be significantly reduced. In specific embodiments, the ionic liquid active can form a liquid composition in "supercompact" form, i.e., containing no other solvent or diluent in addition to the ionic liquid, or in a "compact" form, containing only a minor portion of solvent or diluent in addition to the ionic liquid.

In one embodiment, the composition is a "supercompact" composition that is substantially non-aqueous, that is, the composition is substantially free of added water. As used herein, the term "added water" or "free water" refers to refers to the free, unbounded water that is intentionally added to the composition. The substantially non-aqueous compositions can contain less than about 10 weight percent, more specifically less than about 5 weight percent, even more specifically less than about 1 weight percent, added water. It is recognized that many ionic liquids are hygroscopic, thus, may contain appreciable amounts of water (referred to herein as the "innate" or "bound" water) ranging from about 0.01% to about 50%, preferably from about 0.1% to about 20%, by weight of the ionic liquid. It is recognized that once the composition is prepared, the water component (innate water or added water) can no longer be distinguished by its origin. Thus, the compositions of the present invention may comprise water, regardless of its origin, ranging from about 0.01% to about 50%, preferably from about 1% to about 40%, more preferably from about 5% to about 30%, even more preferably less than 10% by weight of the composition.

In additional embodiments, the "compact" compositions of the present invention contain a minor portion of water or other solvents, and the balance, ionic liquid actives. Such minor portion may be, for example, less than about 20%, alternatively, less than about 10%, further alternatively, less than about 5%, by weight of the composition.

The compositions of the present invention have a viscosity less than about 5000 mPa·s. In another embodiments, the viscosity of such composition is less than about 2000 mPa·s at room temperature (about 20° C.). In still another embodiment, the viscosity of such compositions lower to less than about 2000 mPa·s, preferably less than about 500 mPa·s, and more preferably less than about 300 mPa·s, when heated to a temperature in the range of about 40° C. to 60° C. In some embodiments, the compositions of the present invention have a melting point less than 100° C.

In a further embodiment, a composition according to the invention, comprising an ionic liquid active composed of a first ion active and an ionic liquid-forming counter ion, can be combined with another one or more additional ion actives to provide a liquid composition having additional treating benefits. The first ion active and the additional ion active(s) may be the same or different and may provide the same of different benefit properties.

The compositions may optionally include a solvent. Typical examples of solvents include, but are not limited to, linear or branched C1-C10 alcohols, diols, and mixtures thereof. In specific embodiments, solvents such as ethanol, isopropanol, propylene glycol are used in the compositions of the present invention.

In some embodiments, the composition is a clear liquid because any dispersed phase therein has a dimension less than the wavelength of visible light. In other embodiments, the clear compositions may comprise a homogeneous single phase in which the ionic liquid is dissolved or incorporated into a conventional aqueous phase, either in situ or with an optional surfactant added to the composition. Alternatively, the clear compositions may comprise a two phase liquid system in which the ionic liquids are dispersed in the conventional aqueous phase wherein ionic liquid droplets have a density and refractive index matched to the continuous phase. In further embodiments, the composition is a two phase liquid system having visibly separated aqueous phase and ionic liquid phase.

The compositions may comprise the ionic liquid active in any amount suitable for the desired functionality. In a specific embodiment, the compositions comprise the ionic liquid active in an amount of from about 1 to about 75 weight percent, more specifically from about 1 to about 40 weight percent, even more specifically from about 1 to about 20 weight percent of the compositions. Typically, the present compositions allow inclusion of greater amounts of active in a liquid form as compared with conventional compositions employing actives in conventional solid forms. Thus, in one specific embodiment, the composition may be in the form of a "supercompact" composition, comprising about 50% to 100%, or from about 75% to about 99% of the ionic liquid active, the balance adjuncts and/or water. In an alternative embodiment, the composition is in the form of a concentrated or compact composition, comprising from about 50% to about 95% or from about 60% to about 80% by weight of the ionic liquid active.

The compositions of the present invention may be provided in various forms, including, but not limited to, hand dishwashing detergents, automatic dishwashing detergents, pretreating compositions, hand laundry detergents, automatic laundry detergents, and the like. The ionic liquid compositions may be formulated in the form of liquid, gel, paste, foam, or solid. When the composition is in the solid form, it can be further processed into granules, powders, tablets, or bars. The composition may be employed as a component of another cleaning product, for example by application to an absorbent substrate to provide a wipe for use in various applications. Any suitable absorbent substrate may be employed, including woven or nonwoven fibrous webs and/or foam webs. It is preferred that such an absorbent substrate should have sufficient wet strength to hold an effective amount of the composition according to the present invention to facilitate cleaning.

The invention therefore encompasses unit dose products, which typically employ a composition of the present invention in a unit dose package comprising a water soluble polymer film. Unit dose package such as those disclosed in U.S. Pat. Nos. 4,973,416; 6,451,750; 6,448,212; and U.S. 2003/0,054,966A1, are suitable for use with the composition of the present invention. The embodiments containing little or no water (e.g., the supercompact composition) may be advantageous for improving the stability of unit dose packaged materials and products.

The compositions according to the invention may additionally include one or more conventional fabric, surface and/or air treating adjunct components, as desired. Suitable adjunct components include, but are not limited to, additional detersive surfactants and builders (such as silicas, zeolites, phosphates, polacrylates, poly(acrylic-maleic) copolymers), enzymes, enzyme stabilizers (such as propylene glycol, boric acid and/or borax), suds suppressors, soil suspending agents, soil release agents, other fabric treating benefit agents such as anti-abrasion agents, wrinkle resistant agents, stain resistant agents, and water resistant agents, flame retardants, antimicrobial agents, metal bleach catalysts, bleaching agents, softeners, anti-pilling agents, water repellant agents, ultraviolet protection agents, pH adjusting agents, chelating agents, smectic clays, solvents, hydrotropes and phase stabilizers, structuring agents, dye transfer inhibiting agents, sizings, perfumes, coloring agents, mixtures thereof, i.e., of two or more of these components, and the like. Additional examples of suitable components are disclosed in U.S. Pat. No. 6,488,943, Beerse et al.; U.S. Pat. No. 6,514,932, Hubesch et al; U.S. Pat. No. 6,548,470, Buzzaccarini et al.; U.S. Pat. No. 6,482,793, Gordon et al.; U.S. Pat. No. 5,545,350, Baker et al; U.S. Pat. No. 6,083,899, Baker et al; U.S. Pat. No. 6,156,722, Panandiker et al; U.S. Pat. No. 6,573,234, Sivik et al.; U.S. Pat. No. 6,525,012, Price et al.; U.S. Pat. No. 6,551,986, Littig et al; U.S. Pat. No. 6,566,323, Littig et al.; U.S. Pat. No. 6,090,767, Jackson et al.; and/or U.S. Pat. No. 6,420,326, Maile et al.

The various optional composition ingredients, if present in the compositions herein, should be utilized at concentrations conventionally employed to bring about their desired contribution to the composition. Frequently, the total amount of such optional composition ingredients can range from about 0.01% to about 50%, more preferably from about 1% to about 30%, by weight of the composition.

The compositions are easily diluted with water and/or organic solvent, without formation a gel phase during the dilution process. As used herein, the term "gel phase" is defined as a phase region in which the composition exhibits a significant (e.g., at least 10%) increase in viscosity upon dilution. Accordingly, the invention is further directed to processes for diluting compositions.

In one embodiment, when the product formulation is used by a consumer, for example, to form a wash liquor for laundry or dish washing (typically a dilution with water of greater than 1:100), the product formulation easily disperses into the diluting water and/or solvent with little stirring or time lapse since no gel phase is formed when the product formulation is first added to the diluting water and/or solvent. The process for diluting a composition to prepare a wash liquor comprises: a) providing a composition comprising an ionic liquid active, and b) diluting the composition by addition of water and/or an organic solvent. Advantageously, the composition does not exhibit a gel phase throughout the dilution process.

The avoidance of gel phase formation provides various benefits to the compositions of the invention. For example, when the ionic liquid active is mixed with other components to form a consumer product formulation, the mixing step effects dispersion of ionic liquid active and a significant initial increase in viscosity is avoided since no gel phase is formed.

EXAMPLES

In this example, a composition according to the invention is prepared. A fabric softener active comprising [DCEEDMA$^+$][Cl$^-$] of the formula:

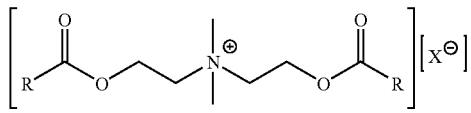

wherein R is canola and X is Cl, has a melting point of about 55° C. and a viscosity of about 8000 mPa·s at 70° C. and about 37,000 mPa·s at 55° C., which presents challenging formulation processing. According to the present invention, the chloride ion of the active is exchanged with 1,1,1-trifluoro-N-[(trifluoromethyl) sulfonyl] methanesulfonamidinate [NTf$_2$]$^-$ to produce the compound [DCEEDMA][NTf$_2$]. This compound is then added to ionic liquid comprising the pyrrolidinium salt [C$_4$MePyr][NTf$_2$] in a 9:1 weight ratio (0.954: 0.046 molar ratio). The resulting mixture has a dramatically lower viscosity of about 250 mPa·s at 55° C. The viscosity increases slightly as the temperature is lowered but remains below 2000 mPa·s at room temperature.

Additional examples include fabric softener active having the same general formula ([DCEEDMA$^+$][X$^-$]) as above, wherein R is canola or tallow and X is adipate, aspartate, benzoate, citrate, docusate, gluconate, lactate, maleate, phosphate, alkyl phosphonate, phthalate, sarcosinate, succinate, alkylene succinate, tartrate, or tosylate.

In another example, the composition of the present invention may comprise surfactant-derived ion active and ionic liquid-forming counterions. Examples of such surfactant-derived ionic liquids are described in detail in co-filed patent applications Ser. Nos. 60/624,056 and 60/624,125 (P&G case 9817P and 9818P).

Formulation Examples

A. The following are examples of supercompact composition containing fabric softener ions:

| Component | 1 | 2 |
|---|---|---|
| [DCEEDMA] [NTf$_2$] | 96.75 | 94.95 |
| Fatty acid | — | 1.0 |
| Dispersant polymer | 0.60 | 0.40 |
| PEG | 1.5 | 2.5 |
| Perfume | 1.0 | 1.0 |
| Silicone suds suppressor | 0.15 | 0.15 |
| Electrolyte | — | 600 ppm |
| Dye | 50 ppm | 50 ppm |

B. The following are examples of composition containing fabric softener ions:

| Component | 3 | 4 | 5 | 6 |
|---|---|---|---|---|
| [DCEEDMA] [NTf$_2$] | 14.0 | 18.0 | 25.0 | 20.0 |
| Fatty acid | — | 1.0 | — | 1.0 |
| Hydrochloric acid | 0.05 | 0.05 | 0.05 | 0.5 |
| Dispersant polymer | 0.06 | 0.15 | 0.60 | 0.4 |
| Perfume | 1.6 | 1.4 | 1.2 | 1.3 |
| Silicone suds suppressor | 0.15 | 0.15 | 0.15 | 0.15 |
| Eletrolyte | 600 ppm | 600 ppm | 600 ppm | 600 ppm |
| Dye | 50 ppm | 50 ppm | 50 ppm | 50 ppm |
| Water | balance | balance | balance | balance |

C. The following are examples of compositions containing anionic surfactant ion actives:

| Component (wt %) | 7 | 8 | 9 | 10 | 11 |
|---|---|---|---|---|---|
| Ionic Liquid 1[a] | — | 5 | — | — | — |
| Ionic Liquid 2[b] | 10 | — | — | — | 60 |
| Ionic Liquid 3[c] | — | — | 20 | 2 | — |
| Aesthetic Agents[1] | 1 | 1 | 1 | 1 | 1 |
| Enzymes[2] | 2 | — | — | 1 | — |
| Adjuncts[3] | 40 | 30 | 10 | 25 | 5 |
| Co-solvent[4] | — | 5 | 2 | — | 15 |
| Phase stabilizing surfactants | 0.5 | 1 | 0 | 2 | 3 |
| Water | balance | balance | balance | balance | balance |

[a]Trioctyl methyl amine dioctyl Sulfosuccinate;
[b]Triisooctyl methyl amine C$_{12-13}$ methyl branched dodecyl sulfate;
[c]Tetraoctyl amine dodecyl sulfate.

D. The following are examples of compositions containing amphoteric surfactant ion actives:

| Composition (wt %) | 12 | 13 | 14 | 15 | 16 | 17 |
|---|---|---|---|---|---|---|
| Ionic Liquid 4[d] | — | 5 | — | 2 | — | — |
| Ionic Liquid 5[e] | 10 | — | — | — | 60 | — |
| Ionic Liquid 6[f] | — | — | 20 | — | — | 90 |
| Aesthetic Agents[1] | 1 | 1 | 1 | 1 | 1 | 1 |
| Enzymes[2] | 2 | — | — | 1 | — | — |
| Adjuncts[3] | 40 | 30 | 10 | 25 | 5 | 5 |
| Co-solvent[4] | — | 5 | 2 | — | 15 | 2 |
| Water | balance | balance | balance | balance | balance | balance |

[d]N-dodecyl-N,N-dimethyl-N-hydroxyammonium dodecylethoxysulfate;
[e]N-(dodecylamidopropyl)-N,N-dimethyl-N-carboxymethylammonium;
[f]N-decyl-N,N-dimethyl-N-hydoxyammonium 2,4,8-trimethylnonyl-6-(triethoxysulfate).

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid supercompact composition comprising from 75% to 99% by weight of an ionic liquid fabric softener active of the formula:

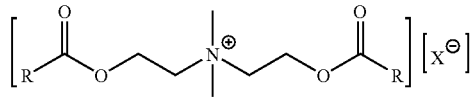

wherein R is canola or tallow and X is a member selected from the group consisting of 1,1,1-trifluoro-N-[(trifluoromethyl) sulfonyl] methanesulfonamidinate, wherein the composition comprises less than about 10% by weight of added water and wherein the composition is substantially non-aqueous.

2. The composition of claim 1, wherein the composition has a viscosity less than about 5000 mPa·s at room temperature or less than about 2000 mPa·s at a temperature in the range of about 40° C. to about 60° C.

3. A unit dose product, comprising a unit dose package and the composition of claim 1 contained in the package.

4. A composition according to claim 1 wherein R is canola and X is 1,1,1-trifluoro-N-[(trifluoromethyl) sulfonyl] methanesulfonamidinate.

* * * * *